(12) United States Patent
Hanabusa

(10) Patent No.: US 8,671,771 B2
(45) Date of Patent: Mar. 18, 2014

(54) BIAXIAL TENSILE TESTING MACHINE

(75) Inventor: Yasuhiro Hanabusa, Gotemba (JP)

(73) Assignee: Mitsubishi Materials Corporation, Tokyo (JP)

( * ) Notice: Subject to any disclaimer, the term of this patent is extended or adjusted under 35 U.S.C. 154(b) by 243 days.

(21) Appl. No.: 13/255,312

(22) PCT Filed: Mar. 10, 2010

(86) PCT No.: PCT/JP2010/001706
§ 371 (c)(1),
(2), (4) Date: Sep. 8, 2011

(87) PCT Pub. No.: WO2010/103830
PCT Pub. Date: Sep. 16, 2010

(65) Prior Publication Data
US 2011/0314926 A1 Dec. 29, 2011

(30) Foreign Application Priority Data
Mar. 10, 2009 (JP) ................. 2009-057143

(51) Int. Cl.
*G01N 3/08* (2006.01)
(52) U.S. Cl.
USPC ........................ 73/826; 73/862.041
(58) Field of Classification Search
USPC ............. 73/760, 826, 862.041–862.046
See application file for complete search history.

(56) References Cited

U.S. PATENT DOCUMENTS

| | | | | |
|---|---|---|---|---|
| 4,955,948 A | * | 9/1990 | Focke et al. ................. | 131/280 |
| 5,215,948 A | * | 6/1993 | Egerton et al. .............. | 501/134 |
| 5,448,918 A | * | 9/1995 | Tucchio ...................... | 73/819 |
| 5,905,205 A | * | 5/1999 | Clay ........................... | 73/856 |
| 6,487,902 B1 | * | 12/2002 | Ghosh .......................... | 73/159 |
| 6,564,646 B1 | | 5/2003 | Gerlach et al. | |
| 7,712,379 B2 | * | 5/2010 | Abu-Farha et al. ........... | 73/856 |
| 8,061,214 B2 | * | 11/2011 | Liggett et al. ................. | 73/788 |

FOREIGN PATENT DOCUMENTS

| | | |
|---|---|---|
| JP | 53-098890 A | 8/1978 |
| JP | 61-114836 A | 6/1986 |
| JP | 05-180743 A | 7/1993 |
| JP | 06-109609 A | 4/1994 |

(Continued)

OTHER PUBLICATIONS

Toshihiko Kuwabara et al., "Measurement and Analysis of Contours of Plastic Work in Cold Rolled Sheet Steel by Biaxial Tensile Tests Using Cruciform Specimens," Journal of Japan Society for Technology of Plas., vol. 40, No. 457 (Feb. 1999), pp. 61-65 and partial translation thereof.

(Continued)

*Primary Examiner* — Max Noori
(74) *Attorney, Agent, or Firm* — Edwards Wildman Palmer LLP

(57) ABSTRACT

A biaxial tensile testing machine performing a tensile test of a test piece by stretching the test piece in four directions along two axes perpendicular to each other includes: first and second turntables which are disposed so as to be parallel to each other and relatively rotatable about a rotary axis along the planer direction thereof; first to fourth link mechanisms which are provided at 90° intervals in the circumferential direction about the rotary axis so that one ends of respective members of a pair of members are rotatably connected to each other, and the other ends of respective members of the pair of members are attached across the first and second turntables; and first to fourth test piece holding units which are respectively attached to the first to fourth link mechanisms and hold the test piece.

6 Claims, 8 Drawing Sheets

(56) References Cited

FOREIGN PATENT DOCUMENTS

| JP | 2000-180322 A | 6/2000 |
|----|---------------|--------|
| JP | 2000-514179 A | 10/2000 |
| JP | 2003-207430 A | 7/2003 |
| JP | 2004-017367 A | 1/2004 |
| JP | 2009-244183 A | 10/2009 |
| JP | 2010-014612 A | 1/2010 |

OTHER PUBLICATIONS

International Search Report dated May 18, 2010, issue for PCT/JP2010/001706.

* cited by examiner

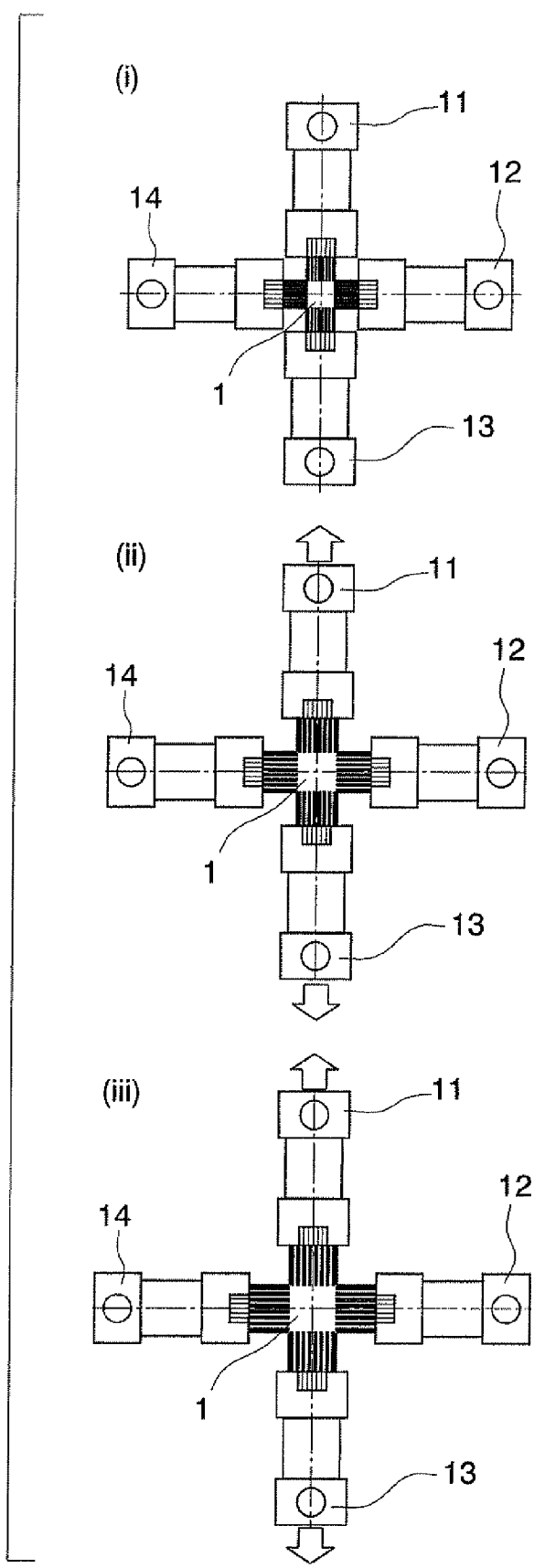

BIAXIAL TENSILE TESTING MACHINE

TECHNICAL FIELD

The present invention relates to a tensile testing machine used for a biaxial tensile test of a thin sheet material, and particularly, to a biaxial tensile testing machine capable of performing a biaxial tensile test through simple means using a uniaxial tensile testing device. Priority is claimed on Japanese Patent Application No. 2009-57143, filed Mar. 10, 2009, the content of which is incorporated herein by reference.

BACKGROUND ART

Hitherto, as a biaxial tensile testing machine, techniques disclosed in PTL 1 and NPL 1 are widely known. In the biaxial tensile testing machines disclosed in the Patent Literature, four gripping jigs gripping a thin sheet test piece are respectively fixed to tensile test shafts of two hydraulic cylinders disposed on each of two axes perpendicular to each other in order to stretch the cross-shaped thin sheet test piece in four directions. According to the biaxial tensile testing machine, when the four hydraulic cylinders are driven, the thin sheet test piece gripped by the gripping jigs is stretched in four directions, whereby a biaxial tensile test is performed on the thin sheet test piece.

CITATION LIST

Patent Literature

[PTL 1] Japanese Patent Application Laid-Open No. 6-109609

Non-Patent Literature

[NPL 1] JOURNAL OF JAPAN SOCIETY FOR TECHNOLOGY OF PLAS, Vol. 40, No. 457 (1999-2), Pages 145 to 149 "measurement and formulation of surface deflection of cold-rolled steel sheet by biaxial tensile test using cross-shaped test piece"

SUMMARY OF INVENTION

Technical Problem

In such a biaxial tensile testing machine, since four hydraulic cylinders are necessary, it is difficult to drive the four hydraulic cylinders in a synchronized manner or perform axis alignment or the like between two hydraulic cylinders on each of two axes perpendicular to each other.

On the other hand, in the technique disclosed in NPL 1, pressure oil is supplied from the same hydraulic source to two hydraulic cylinders disposed on the same axis in the hydraulic cylinders disposed on the axes perpendicular to each other, and the displacements of two hydraulic cylinders disposed on the same axis are forcedly set to be equal to each other by an equal-displacement mechanism such as a pantograph. However, even in this case, there is a need to synchronize displacements between the hydraulic cylinders disposed on the axes perpendicular to each other.

The invention is made in view of the above-described circumstances, and it is an object of the invention to provide a biaxial tensile testing machine capable of performing a tensile test in four directions along two axes perpendicular to each other even by driving unit such as one hydraulic cylinder, synchronizing stretching operations in four directions, and having a simple configuration and a small number of components since the axis alignment or the like between the axes perpendicular to each other in the existing mechanism using four hydraulic cylinders is not needed.

Solution to Problem

In order to solve the above-described problems, the invention proposes the following means. A biaxial tensile testing machine performing a tensile test of a test piece by stretching the test piece in four directions along two axes perpendicular to each other includes: first and second turntables which are disposed so as to be parallel to each other and relatively rotatable about a rotary axis along the planer direction thereof; first to fourth link mechanisms which are provided at 90° intervals in the circumferential direction about the rotary axis so that one ends of respective members of a pair of members are rotatably connected to each other, and the other ends of respective members of the pair of members are attached across the first and second turntables; and first to fourth test piece holding units which are respectively attached to the first to fourth link mechanisms and hold the test piece.

In the biaxial tensile testing machine with the above-described configuration, when one ends of any one of the first and third link mechanisms or the second and fourth link mechanisms facing each other, for example the first and third link mechanisms are moved in the direction moving away from each other by driving unit, the first and second turntables are respectively rotated in accordance with the deformation of the first and third link mechanisms. By the rotation of the first and second turntables, the second and fourth link mechanisms facing each other move in the direction moving away from each other. In this manner, the first and third link mechanisms and the second and fourth link mechanisms respectively disposed at positions facing each other move in the directions moving away from each other.

Therefore, it is possible to simultaneously move the first to fourth test piece holding units respectively attached to the first to fourth link mechanisms in four directions along two axes perpendicular to each other. Accordingly, it is possible to perform a tensile test on the test piece held by the test piece holding units in four directions. Further, in such a biaxial tensile test, since a universal uniaxial testing machine may be used as driving unit, it is possible to manufacture the device at low cost. Further, the stretching operation in four directions may move the first and third link mechanisms and the second and fourth link mechanisms to be synchronized with each other. Further, a troublesome axis alignment or the like such as in the existing mechanism using four driving devices is not needed. Furthermore, it is possible to simplify the structure of the device.

The shapes of the first turntable and the second turntable may be the same.

In this case, since the first and second turntables have the same shape, it is possible to easily manufacture the first and second turntables and manage the components thereof.

The first to fourth test piece holding units may be respectively attached to shafts rotatably connecting one ends of the pair of members constituting the first to fourth link mechanisms.

In this case, the shaft connecting one ends of the pair of members has two functions, that is, a function of rotatably connecting one ends of the pair of members to each other and a function of supporting the test piece holding units. For this reason, it is possible to decrease the number of components and simplify the configuration.

The first to fourth test piece holding units each may include a gripping portion gripping the end of the test piece, a support portion connected to each shaft of the first to fourth link mechanisms, and biasing unit provided between the gripping portion and the support portion.

In this case, when an elastic coefficient (for example, a spring constant) of the biasing unit provided between the gripping portion and the support portion is appropriately set, displacement may be converted into a load, which enables a tensile test on a test piece in four directions along two axes through a load control.

Advantageous Effects of Invention

According to the biaxial tensile testing machine of the invention, it is possible to simultaneously move the first and third link mechanisms and the second and fourth link mechanisms in the directions moving away from each other by the rotation of the first and second turntables. For this reason, for example, it is possible to perform a tensile test in four directions along two axes perpendicular to each other using driving unit, for example, one hydraulic cylinder and perform the stretching operations in four directions in a synchronized manner. As a result, the axis alignment or the like between the axes perpendicular to each other such as in the mechanism using four driving devices is not needed, and the structure of the device may be simplified.

Furthermore, since the motions of the first and third link mechanisms are transmitted to the second and fourth link mechanisms by using the first and second turntables, for example, compared to a structure in which two pantographs are connected to each other through connection means and a tensile test is performed on a test piece by synchronizing the deformation of the pantographs, it is possible to decrease the number of components and further simplify the configuration.

BRIEF DESCRIPTION OF DRAWINGS

FIG. 5B is a diagram illustrating operations (i) to (iii) of test piece holding units 11 to 14 of the first embodiment.

DESCRIPTION OF EMBODIMENTS

First Embodiment

Figure 1:
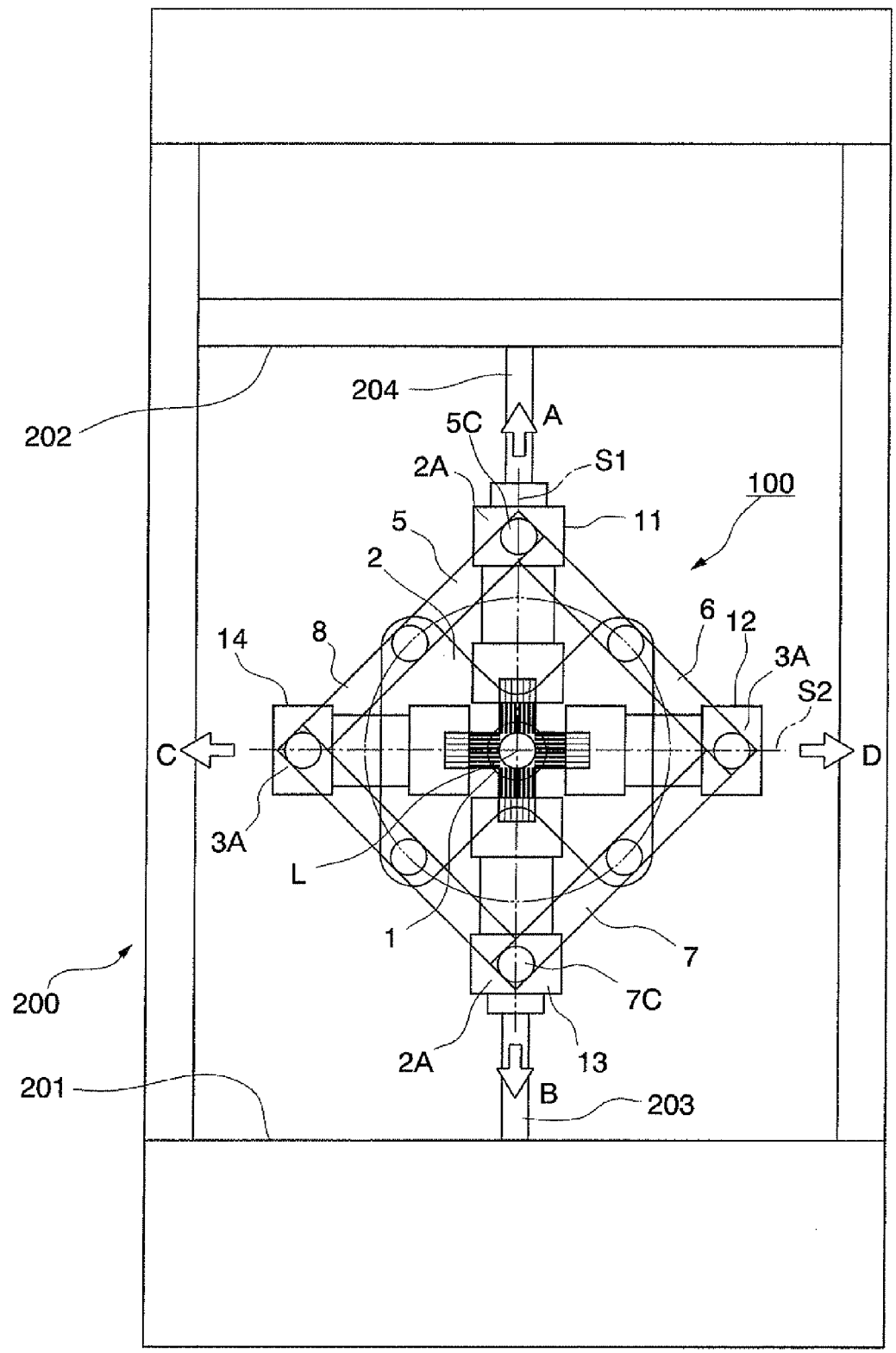
FIG. 1 is a front view illustrating a state where a biaxial tensile testing machine according to a first embodiment of the invention is assembled to a uniaxial tensile testing device.

A first embodiment of the invention will be described by referring to FIGS. 1 to 5B. FIG. 1 is a diagram illustrating a biaxial tensile testing machine 100 that performs a tensile test by stretching a cross-shaped test piece 1 in four directions (directions depicted by the arrows A, B, C, and D) along two axes (depicted by axes S1 and S2) perpendicular to each other. As shown in FIG. 1, the biaxial tensile testing machine 100 is used while being assembled to, for example, a uniaxial tensile testing device 200.

Specifically, in the biaxial tensile testing machine 100, a lower side front end (specifically, a shaft 7C to be described later) on one axis S1 extending up and down is connected to a base 201 of the uniaxial tensile testing device 200 through a connection rod 203, and an upper side front end (specifically, a shaft 5C to be described later) on the axis S1 is connected to a movable plate 202 of the uniaxial tensile testing device 200 through a connection rod 204. The left and right ends of the biaxial tensile testing machine 100 are respectively free.

The movable plate 202 is movable up and down by, for example, driving unit such as a ball screw mechanism driven by a motor.

Figure 2A:
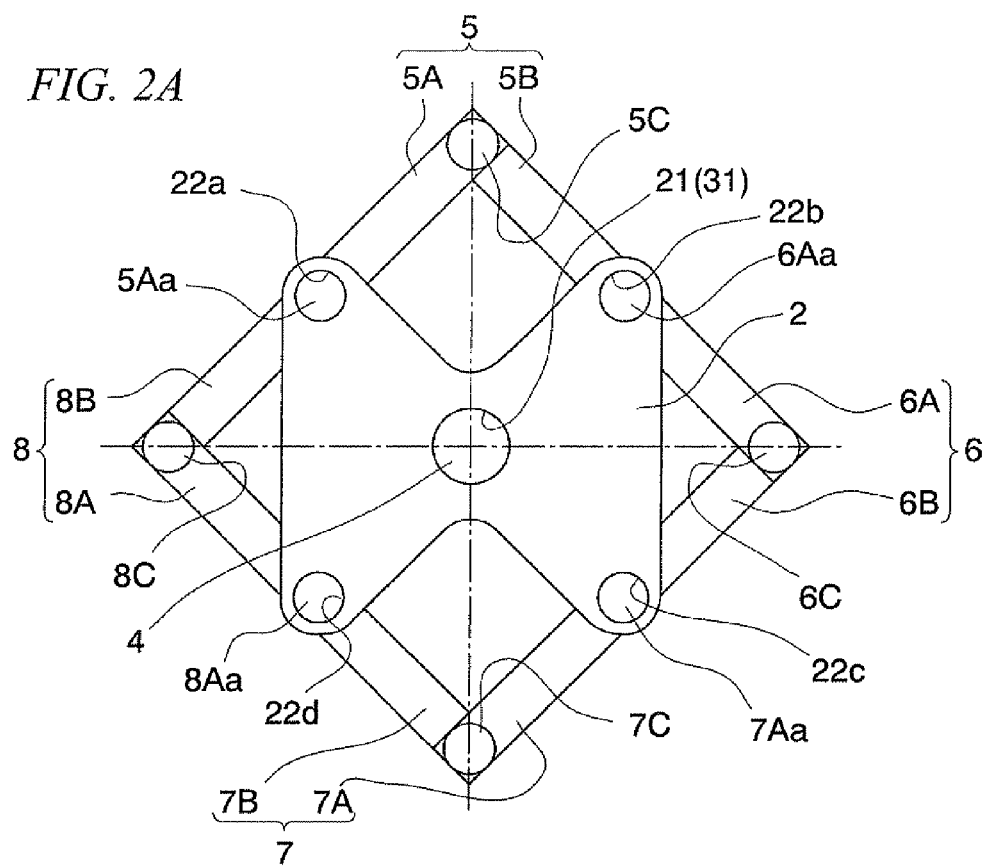
FIG. 2A is a front view illustrating an entire part of the biaxial tensile testing machine of the first embodiment, and is a front view of a part including first and second turntables 2 and 3 and first to fourth link mechanisms 5 to 8.
Figure 4:
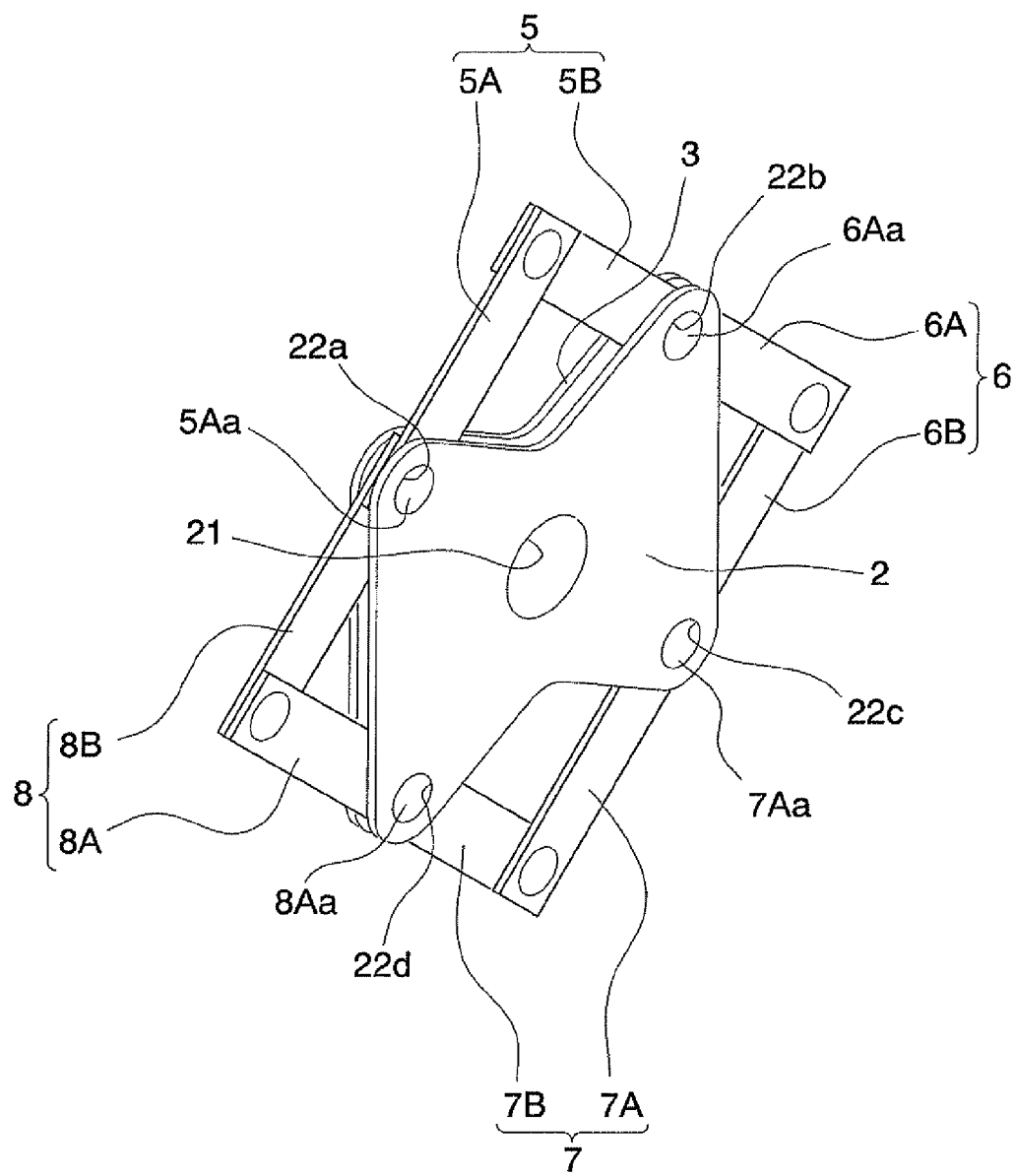
FIG. 4 is a perspective view of a part including the first and second turntables 2 and 3 and the first to fourth link mechanisms 5 to 8 of the biaxial tensile testing machine 100.

As shown in FIGS. 1, 2A, and 4, the biaxial tensile testing machine 100 includes first and second turntables 2 and 3 that are disposed to be parallel to each other and are rotatable about a shaft 4 along the plane direction thereof and first to fourth link mechanisms 5 to 8 that are provided at 90° intervals in the circumferential direction about the rotary axis L of the first and second turntables 2 and 3.

Figure 2B:
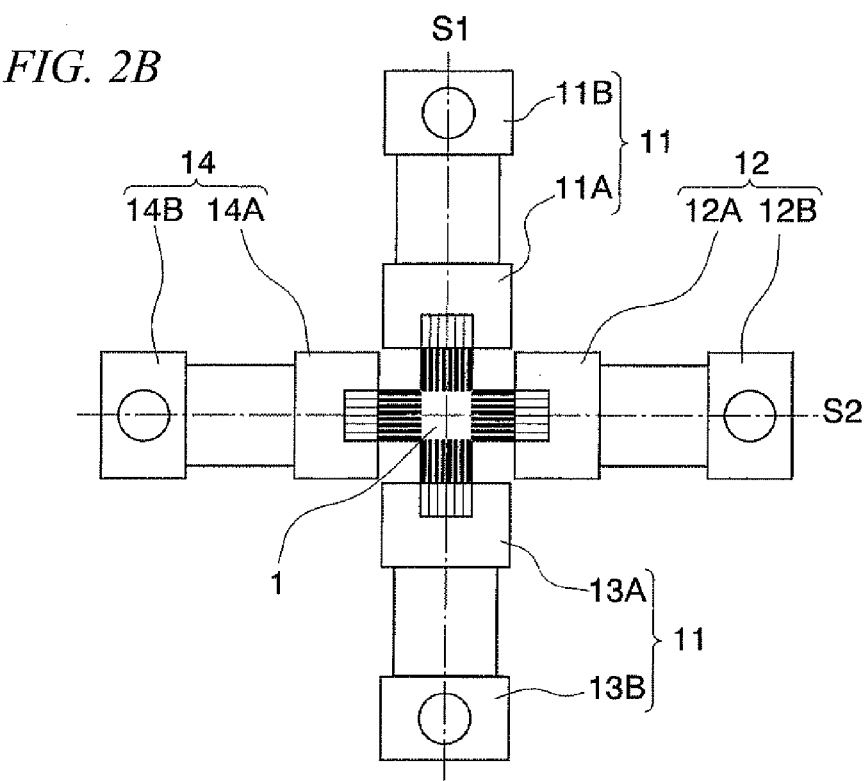
FIG. 2B is a front view illustrating an entire part of the biaxial tensile testing machine of the first embodiment, and is a front view of a part of first to fourth test piece holding units 11 to 14.

The front end positions (denoted by the reference numerals 2A and 3A) of the axes S1 and S2 respectively connecting the upper link mechanism 5 to the lower link mechanism 7 and the right link mechanism 6 to the left link mechanism 8 are respectively attached with first to fourth test piece holding units 11 to 14 that are used to hold the cross-shaped test piece 1 as shown in FIGS. 1 and 2B. Further, the cross-shaped test piece 1 is provided with slits that are provided in four directions so that a portion other than the center portion of the test piece does not act as a deformation resistance against loads in the directions perpendicular to each other in the test piece 1 during a stretching operation.

The first turntable 2 has a shape in which two right-angled triangles abut against each other so that two peaks forming 90° face each other and lower sides are parallel to each other. In other words, upper and lower portions of a square-shaped plate are respectively provided with notches with a right-angled-triangle shape. The center of the first turntable 2 is provided with a hole 21, and four corners extending outward are provided with holes 22a to 22d which are sequentially provided in the clockwise direction from the left upper corner about the rotary axis L.

The second turntable 3 is also formed in the same shape as that of the first turntable 2. That is, a hole 31 is formed at the center of the second turntable 3, and four corners extending outward are respectively provided with holes 32a to 32d which are sequentially provided in the clockwise direction from the left upper corner about the rotary axis L. The distances from the hole 21 to the holes 22a to 22d are all the same, and the distances from the hole 31 to the holes 32a to 32d are also all the same. Further, the distances from the hole 21 to the holes 22a to 22d are the same as the distances from the hole 31 to the holes 32a to 32d.

The link mechanisms 5 to 8 respectively include a pair of members 5A to 8A and 5B to 8B. In the pair of members 5A to 8A and 5B to 8B, one ends of the members are rotatably connected to each other through the shafts 5C to 8C, and the other ends are attached across the first and second turntables 2 and 3 (refer to FIG. 3B).

Here, in the pair of members 5A to 8A and 5B to 8B of the link mechanisms 5 to 8 described in this specification, the clockwise direction of the rotary axis L is defined as the rightward direction, and counter-clockwise direction of the rotary axis L is defined as the leftward direction.

Specifically, in the upper link mechanism 5, the other end of the left member 5A is rotatably connected to the hole 22a of the left upper corner of the first turntable 2 through a shaft 5Aa, and the other end of the right member 5B is rotatably connected to the hole 32b of the right upper corner of the second turntable 3 through a shaft 5Ba. In the right link mechanism 6, the other end of the left member 6A is rotatably connected to the hole 22b of the right upper corner of the first turntable 2 through a shaft 6Aa, and the other end of the right member 6B is rotatably connected to the hole 32c of the right lower corner of the second turntable 3 through a shaft 6Ba. In the lower link mechanism 7, the other end of the left member 7A is rotatably connected to the hole 22c of the right lower corner of the first turntable 2 through a shaft 7Aa, and the other end of the right member 7B is rotatably connected to the hole 32d of the left lower corner of the second turntable 3 through a shaft 7Ba. In the left link mechanism 8, the other end of the left member 8A is rotatably connected to the hole 22d of the left lower corner of the first turntable 2 through a shaft 8Aa, and the other end of the right member 8B is rotatably connected to the hole 32a of the left upper corner of the second turntable 3 through a shaft 8Ba.

The shafts 5C to 8C connecting one ends of the pair of members to each other and the shafts 5Aa to 8Aa and 5Ba to 8Ba connecting the pair of members and the first and second turntables to each other are respectively disposed to be parallel to the shaft 4 connecting the first and second turntables 2 and 3 to each other.

The pair of members 5A to 8A and 5B to 8B constituting the link mechanisms 5 to 8 respectively have the same length.

Figure 3A:
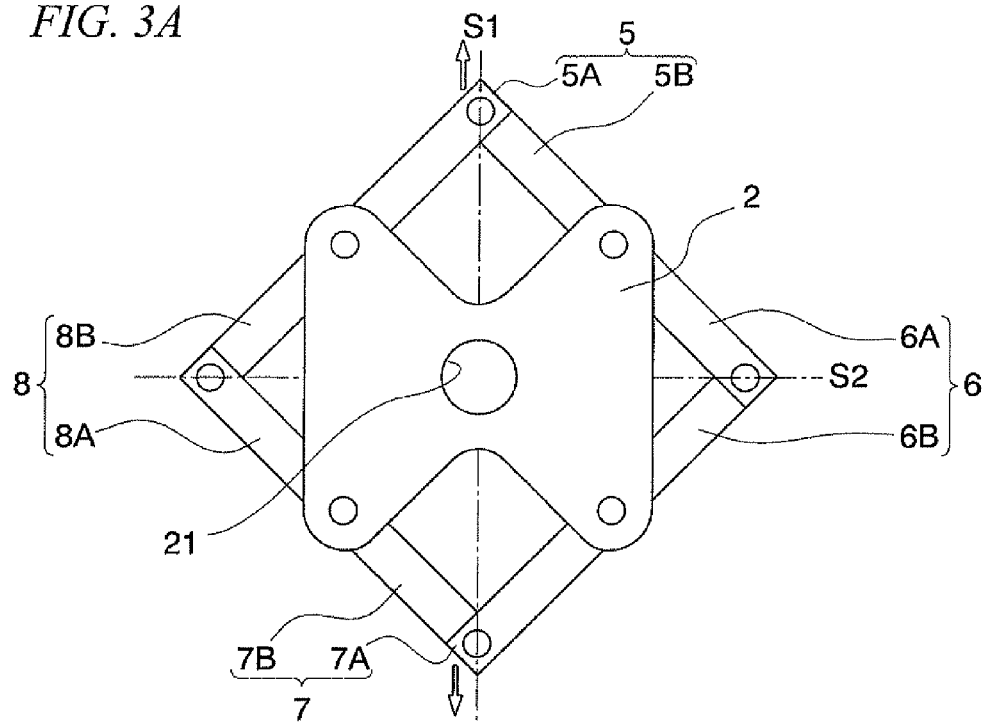
FIG. 3A is a front view specifically illustrating a part including the first and second turntables 2 and 3 and the first to fourth link mechanisms 5 to 8 of the biaxial tensile testing machine 100.
Figure 3B:
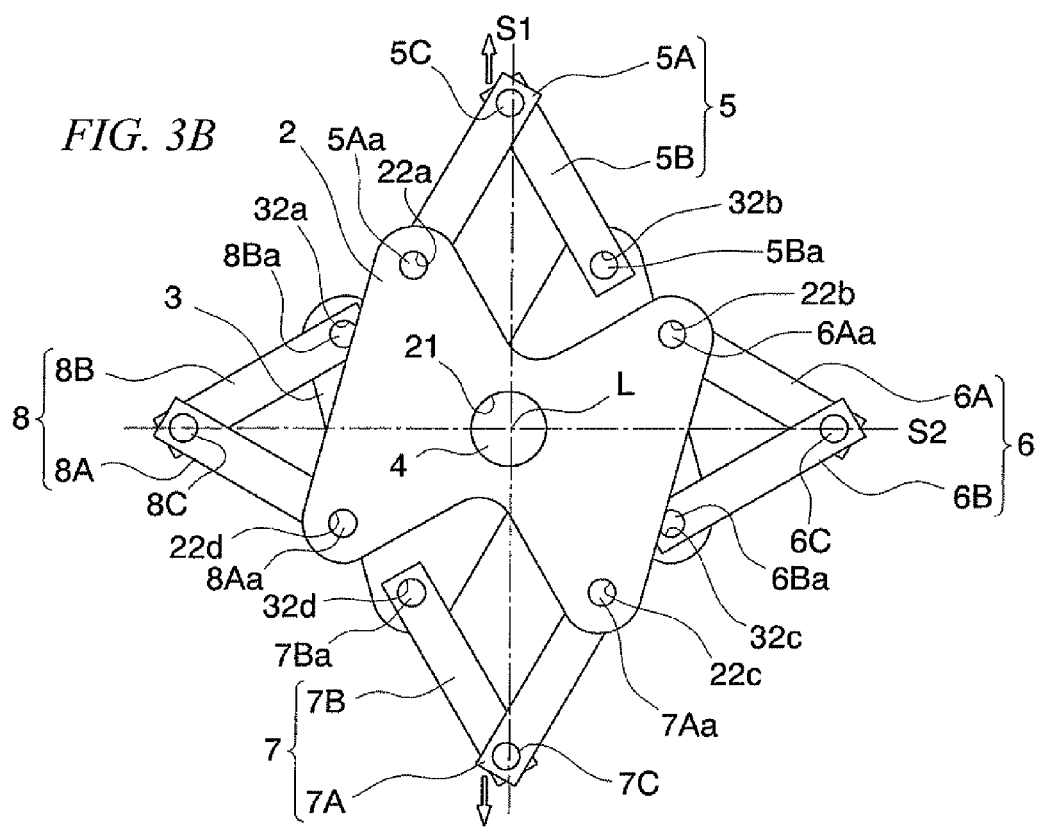
FIG. 3B is a front view illustrating a state where a part including the first and third link mechanisms 5 and 7 of the biaxial tensile testing machine 100 is stretched in the direction moving away from each other by driving unit.

In the embodiment, as respectively shown in FIGS. 2A, 3A, and 3B, the other ends of the members 5A to 8A and 5B to 8B constituting the link mechanisms 5 to 8 are disposed on the inside of the axial direction of the shaft 4 of the first and second turntables 2 and 3, and are connected to be rotatable about the first and second turntables 2 and 3. However, the invention is not limited thereto. The other ends of the members 5A to 8A and 5B to 8B may be disposed on the outside of the axial direction of the shaft 4 of the first and second turntables 2 and 3, and may be connected to be rotatable about the first and second turntables.

As shown in FIG. 2B, the first to fourth test piece holding units 11 to 14 holding the above-described test piece 1 include gripping portions 11A to 14A that grip the end of the cross-shaped test piece 1 and support portions 11B to 14B that respectively connected to the first to fourth link mechanisms 5 to 8. The support portions 11B to 14B are respectively connected to the shafts 5C to 8C that rotatably connect one ends of the pair of members 5A to 8A and 5B to 8B of the first to fourth link mechanisms 5 to 8.

A load cell (not shown) is provided between the test piece 1 and the first and third test piece holding units 11 and 13 along the axis S1 and between the test piece 1 and the second and fourth test piece holding units 12 and 14 along the axis S2 so as to measure respective loads.

Next, an operation of the biaxial tensile testing machine 100 with the above-described configuration will be described.

Figure 5A:
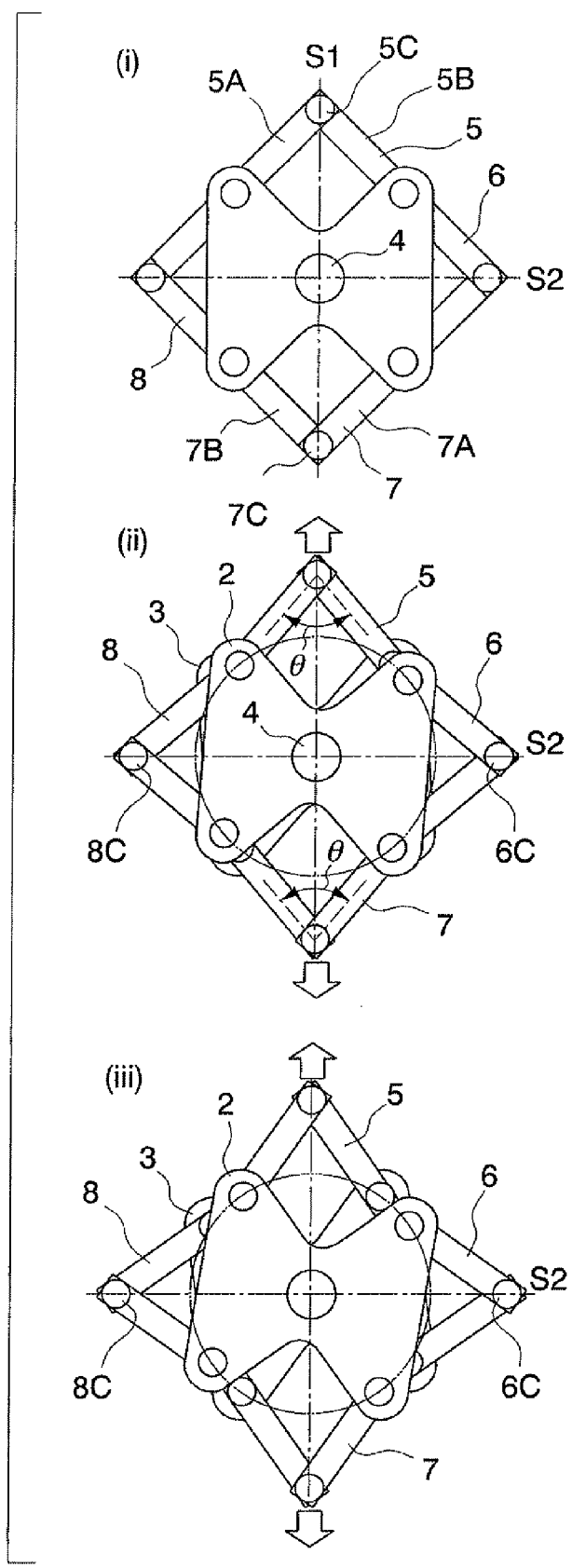
FIG. 5A is a diagram illustrating operations (i) to (iii) of a part including the first and second turntables 2 and 3 and the first to fourth link mechanisms 5 to 8 of the first embodiment.

FIG. 5A illustrates operations (i) to (iii) of a part including the first and second turntables 2 and 3 and the first to fourth link mechanisms 5 to 8. FIG. 5B illustrates operations (i) to (iii) of the first to fourth test piece holding units 11 to 14. As shown in these drawings, when the movable plate 202 of the uniaxial tensile testing device 200 is moved upward by the driving unit, the shaft 5C connecting the pair of members 5A and 5B of the first link mechanism 5 moves upward together with the movable plate 202, and the shaft 7C connecting the pair of members 7A and 7B of the second link mechanism 7 is fixed to the base 201 of the uniaxial tensile testing device, so that the shafts 5C and 7C relatively move along the axis S1 in the direction moving away from each other.

When the shafts 5C and 7C relatively move in this manner, the first and third link mechanisms 5 and 7 respectively connected to the shafts 5C and 7C are deformed, and the deformation is transmitted to the second and fourth link mechanisms 6 and 8 through the first and second turntables 2 and 3.

Specifically, as shown in (ii) of FIG. 5A, the first and third link mechanisms 5 and 7 are deformed so that the other ends of the pair of members 5A and 5B and the other ends of the pair of members 7A and 7B move close to each other. In other words, the first and third link mechanisms 5 and 7 are deformed so that the angle $\theta$ formed by the pair of members 5A and 5B and the angle $\theta$ formed by the pair of members 7A and 7B are narrowed. Accordingly, the first turntable 2 rotates in the clockwise direction about the shaft 4, and the second turntable 3 rotates in the counter-clockwise direction about the shaft 4. In accordance with the rotation of the first and second turntables 2 and 3, the second and fourth link mechanisms 6 and 8 are also deformed so that the other ends of the pair of members 6A and 6B and the other ends of the pair of members 8A and 8B move close to each other. In other words, the second and fourth link mechanisms 6 and 8 are deformed so that the angle $\theta$ formed by the pair of members 6A and 6B and the angle $\theta$ formed by the pair of members 8A and 8B are narrowed. As a result, the shafts 6C and 8C connected to one ends of the second and fourth link mechanisms 6 and 8 relatively move along the axis S2 in the direction moving away from each other.

With the above-described operation, when the shafts 5C and 7C connected to the first and third link mechanisms 5 and 7 are stretched along the axis S1 in the direction moving away from each other, the shafts 6C and 8C simultaneously move along the axis S2 in the direction moving away from each other through the first and third link mechanisms 5 and 7, the first and second turntables 2 and 3, and the second and fourth link mechanisms 6 and 8. As a result, the first to fourth test piece holding units 11 to 14 connected to the shafts 5C, 7C, 6C, and 8C also move in the same direction. For this reason, a tensile test of the test piece 1 attached to the first to fourth test piece holding units 11 to 14 may be performed in four directions along two axes S1 and S2.

In the biaxial tensile testing machine 100 specifically described above, when the shafts 5C and 7C connected to one ends of the upper and lower link mechanisms 5 and 7 between the movable plate 202 and the base 201 relatively move in the direction moving away from each other, the first and third link mechanisms 5 and 7 connected to the shafts 5C and 7C are deformed so as to narrow the angle $\theta$ formed therebetween.

Then, the deformation operation is transmitted to the second and fourth link mechanisms 6 and 8 through the first and second turntables 2 and 3, and the second and fourth link mechanisms 6 and 8 are deformed so as to narrow the angle formed therebetween.

Accordingly, when the shafts 5C and 7C connected to one ends of the upper and lower link mechanisms 5 and 7 are moved in the direction moving away from each other, the operations of the first and third link mechanisms 5 and 7 are transmitted to the second and fourth link mechanisms 6 and 8 through the first and second turntables 2 and 3. Accordingly, the first to fourth test piece holding units 11 to 14 respectively connected to one ends of the first to fourth link mechanisms 5 to 8 may be moved in four directions along two axes S1 and S2 perpendicular to each other. Then, a tensile test of the test piece 1 held by the first to fourth test piece holding units 11 to 14 may be performed in four directions. Accordingly, it is possible to detect deformation characteristics (a relation between stress and strain) of the test piece 1 during the biaxial stretching operation from the load measurement using the load cell and the strain measurement using a strain gauge attached to the test piece in advance.

The stretching operations in four directions may be performed in a synchronized manner by using the first and second turntables 2 and 3 connecting the first and third link mechanisms 5 and 7 and the second and fourth link mechanisms 6 and 8. As a result, the axis alignment of two axes S1 and S2 as in the mechanism using four hydraulic cylinders, is not needed. Further, it is possible to simplify the structure of the device. Furthermore, since the tensile test of the test piece in four directions along two axes S1 and S2 may be performed using a universal uniaxial testing machine, it is possible to manufacture the device at low cost by assembling the link mechanism to the existing uniaxial tensile testing device 200.

Further, since the first and second turntables 2 and 3 are used, for example, compared to a structure in which two pantographs are connected to each other through connection means and a tensile test is performed on a test piece by synchronizing the deformation of the pantographs by using the test piece holding units attached to the corresponding pantographs, it is possible to decrease the number of components and further simplify the configuration.

Further, for example, the lengths of the pair of members 6A and 6B and the pair of members 8A and 8B constituting the second and fourth link mechanisms 6 and 8 may be appropriately changed with respect to the lengths of the pair of members 5A and 5B and the pair of members 7A and 7B constituting the first and third link mechanisms 5 and 7. Accordingly, a tensile test may be performed in which the movement ratio between the driving-side axis S1 and the driven-side axis S2 is changed to change a strain ratio between two axes S1 and S2.

Second Embodiment

Figure 6A:
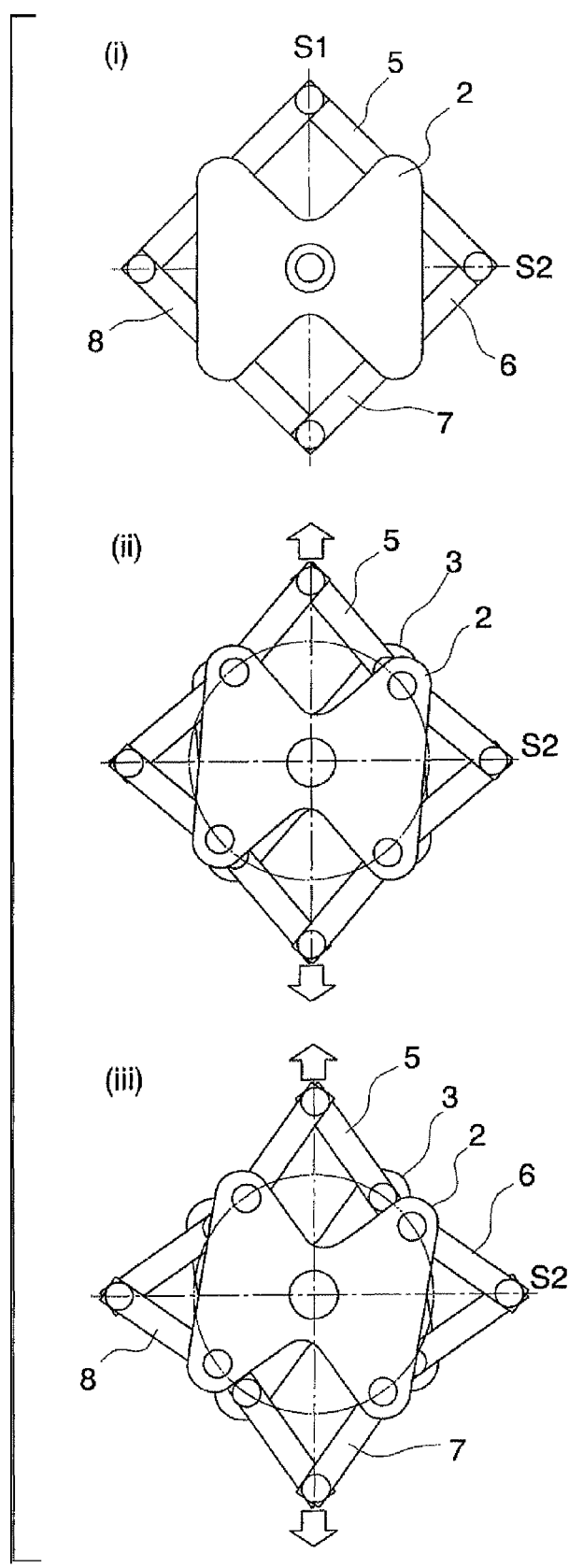
FIG. 6A is a diagram illustrating operations (i) to (iii) of a part including the first and second turntables 2 and 3 and the first to fourth link mechanisms 5 to 8 of a second embodiment.
Figure 6B:
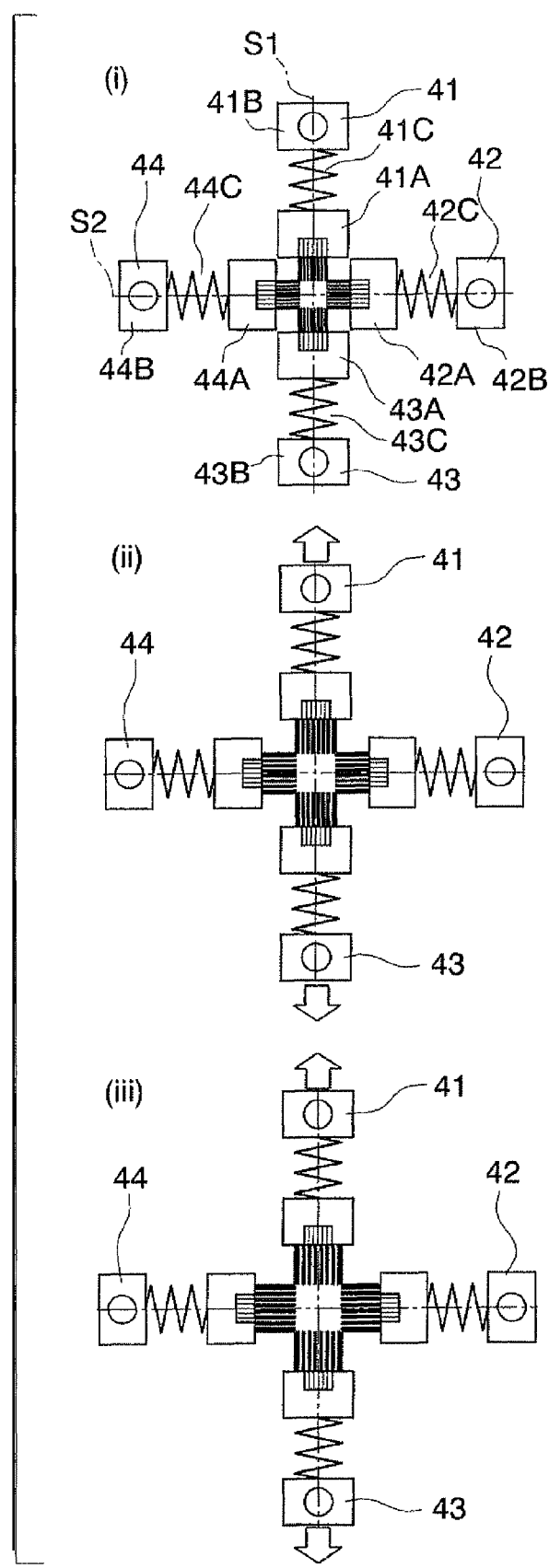
FIG. 6B is a diagram illustrating operations (i) to (iii) of test piece holding units 41 to 44 including tensile springs 41C to 44C of the second embodiment.

FIGS. 6A and 6B illustrate a second embodiment of the invention. FIG. 6A is a diagram illustrating a motion of the first to fourth link mechanisms and the first and second turntables. FIG. 6B is a diagram illustrating a motion of first to fourth test piece holding units 41 to 44 including tensile springs 41C to 44C. In the second embodiment, the same reference numerals will be given to the same components as those of the first embodiment, and a description thereof will not be repeated here.

The second embodiment is characterized in that the first to fourth test piece holding units 41 to 44 include gripping portions 41A to 44A and support portions 41B to 44B which are separated from each other, and tensile springs 41C to 44C are provided between the gripping portions 41A to 44A and the support portions 41B to 44B so as to bias the gripping portions 41A to 44A outward along the axes S1 and S2.

In this manner, when the tensile springs 41C to 44C are provided between the gripping portions 41A to 44A and the support portions 41B to 44B, a test may be performed in which the spring constant of the tensile spring is appropriately changed to change a stress ratio between the driving-side axis S1 and the driven-side axis S2.

While the embodiments of the invention have been described in detail by referring to the drawings, the invention is not limited to the embodiments, and design changes and the like are included in the invention within the scope without departing from the substance of the invention.

For example, in the above-described embodiments, the biaxial tensile testing machine 100 is assembled to the uniaxial tensile testing device 200, the front end of the third link mechanism 7 is fixed, and the front end of the first link mechanism 5 is movable. However, the biaxial tensile testing machine of the invention does not need to be essentially used while being assembled to the uniaxial tensile testing device 200, and a configuration may be adopted in which one or both front ends of the first and third link mechanisms are stretched by the driving unit attached to the frame.

Further, the driving unit is not limited to the motor and the ball screw mechanism, and for example, a hydraulic cylinder or a pneumatic cylinder may be used.

Further, a configuration may be adopted in which guide rails are provided along the axes S1 and S2 and the gripping portions 11A to 14A of the test piece holding units are guided along the guide rails so as to reduce deflection deformation generated in the entire biaxial tensile testing machine.

INDUSTRIAL APPLICABILITY

According to the invention, it is possible to provide a biaxial tensile testing machine capable of performing a tensile test in four directions along two axes perpendicular to each other even by driving unit such as one hydraulic cylinder, synchronizing stretching operations in four directions, and having a simple configuration and a small number of components since the axis alignment or the like between the axes perpendicular to each other as in the existing mechanism using four hydraulic cylinders is not needed.

REFERENCE SIGNS LIST

1: TEST PIECE
2: FIRST TURNTABLE
3: SECOND TURNTABLE
4: SHAFT
5 TO 8: FIRST TO FOURTH LINK MECHANISMS
5A TO 8A: MEMBERS (LEFT MEMBERS)
5B TO 8B: MEMBERS (RIGHT MEMBERS)
5C TO 8C: SHAFTS
41C TO 44C: TENSILE SPRINGS
100: BIAXIAL TENSILE TESTING MACHINE
200: UNIAXIAL TENSILE TESTING DEVICE
S1 AND S2: AXES

The invention claimed is:
1. A biaxial tensile testing machine performing a tensile test of a test piece by stretching the test piece in four directions along two axes perpendicular to each other, the biaxial tensile testing machine comprising:

first and second turntables which are disposed so as to be parallel to each other and relatively rotatable about a rotary axis along the planer direction thereof;

first to fourth link mechanisms which are provided at 90° intervals in the circumferential direction about the rotary axis so that one ends of respective members of a pair of members are rotatably connected to each other, and the other ends of respective members of the pair of members are respectively rotatably connected to the first and second turntables; and first to fourth test piece holding units which are respectively attached to the first to fourth link mechanisms and hold the test piece.

2. The biaxial tensile testing machine according to claim 1, wherein the shapes of the first turntable and the second turntable are the same.

3. The biaxial tensile testing machine according to claim 1, wherein the first to fourth test piece holding units are respectively attached to shafts rotatably connecting one ends of the pair of members constituting the first to fourth link mechanisms.

4. The biaxial tensile testing machine according to claim 3, wherein the first to fourth test piece holding units each include a gripping portion gripping the end of the test piece, a support portion connected to each shaft of the first to fourth link mechanisms, and biasing unit provided between the gripping portion and the support portion.

5. The biaxial tensile testing machine according to claim 2, wherein the first to fourth test piece holding units are respectively attached to shafts rotatably connecting one ends of the pair of members constituting the first to fourth link mechanisms.

6. The biaxial tensile testing machine according to claim 5, wherein the first to fourth test piece holding units each include a gripping portion gripping the end of the test piece, a support portion connected to each shaft of the first to fourth link mechanisms, and biasing unit provided between the gripping portion and the support portion.

* * * * *